US00PP20267P2

(12) United States Plant Patent
Daniëls

(10) Patent No.: US PP20,267 P2
(45) Date of Patent: Sep. 8, 2009

(54) ***THUJA* PLANT NAMED 'DANIELLOW'**

(50) Latin Name: *Thuja plicata*
Varietal Denomination: Daniëllow

(76) Inventor: Albertus Fye Daniëls, Daniëls Boomkwekerij VOF, Barneveldseweg 172 Nijkerk (NL), 3962 PD ( * ) Notice: Subject to any disclaimer, the term of this patent is extended or adjusted under 35 U.S.C. 154(b) by 105 days.

(21) Appl. No.: 11/807,708

(22) Filed: May 29, 2007

(51) Int. Cl.
*A01H 7/00* (2006.01)

(52) U.S. Cl. ..... Plt./213

(58) Field of Classification Search ..... Plt./213, Plt./226
See application file for complete search history.

(56) References Cited

PUBLICATIONS

GTITM UPOVROM Citation for 'Daniellow' as per QZ PBR 20052380; Feb. 15, 2006.*

* cited by examiner

*Primary Examiner*—Kent L Bell

(57) ABSTRACT

A new cultivar of *Thuja plicata* named 'Daniëllow' that is characterized by its upright, conical habit and its bright yellow color throughout the year. In combination these traits set 'Daniëllow' apart from all other existing varieties of *Thuja plicata* known to the inventor.

2 Drawing Sheets

Genus: *Thuja.*
Species: *plicata.*
Denomination: 'Daniëllow'.

BACKGROUND OF THE INVENTION

The present invention relates to a new and distinct cultivar of *Thuja plicata,* commonly known as Western Red Cedar. This plant is grown for use in the landscape as a specimen tree or hedge. The new cultivar is known botanically as *Thuja plicata* and will be referred to hereinafter by the cultivar name 'Daniëllow'.

'Daniëllow' arose and was selected by the inventor at the inventor's nursery in Nijerk, The Netherlands as a naturally occurring single shoot mutation on a single plant of *Thuja plicata* 'Gelderland' (unpatented) in November 1997.

The new *Thuja* variety 'Daniëllow' is an upright tree characterized by bright yellow foliage. This foliage color continues through the summer season. The tree has a tight pyramidal-columnar form that reaches to over 4 meters in the first 10 years.

The closest known comparison plant known to the breeder is the parent plant 'Gelderland'. *Thuja plicata* 'Gelderland' is an upright tree with fragrant deep green foliage that has bronze overtones in the winter. In contrast, *Thuja* 'Dani ëllow' remains bright yellow all year round with a tight pyramidal-columnar form.

The first asexual reproduction of 'Daniëllow' was conducted by the inventor in 1998 in the inventor's propagation greenhouse in Nijkerk, The Netherlands using softwood cuttings. The inventor has since determined that 'Daniëllow' reproduces true to type in all successive generations of asexual reproduction.

SUMMARY OF THE INVENTION

The following traits have been repeatedly observed and represent the characteristics of 'Daniëllow'. These traits in combination distinguish 'Daniëllow' from all other varieties of *Thuja plicata* known to the inventor. 'Daniëllow' has not been tested under all possible conditions and phenotypic differences may be observed with variations in environmental, climatic and cultural conditions, without however, any difference in genotype.

1. 'Daniëllow' has a upright, conical habit.
2. 'Daniëllow' is bright yellow all through the year with no reversion seen.
3. 'Daniëllow' is hardy in Zones 5–8.

BRIEF DESCRIPTION OF THE DRAWINGS

The accompanying two color drawings illustrate the overall appearance of the new cultivar 'Daniëllow' showing the colors as true as it is reasonably possible to obtain in colored reproductions of this type. Colors in the photographs may differ from the color values cited in the detailed botanical description, which accurately describe the actual colors of the new variety of 'Daniëllow'.

The drawing labeled as FIG. 1 illustrates in the foreground a four year old plant of 'Daniëllow' in a field planting of other 'Daniëllow' plants.

Figure 1:
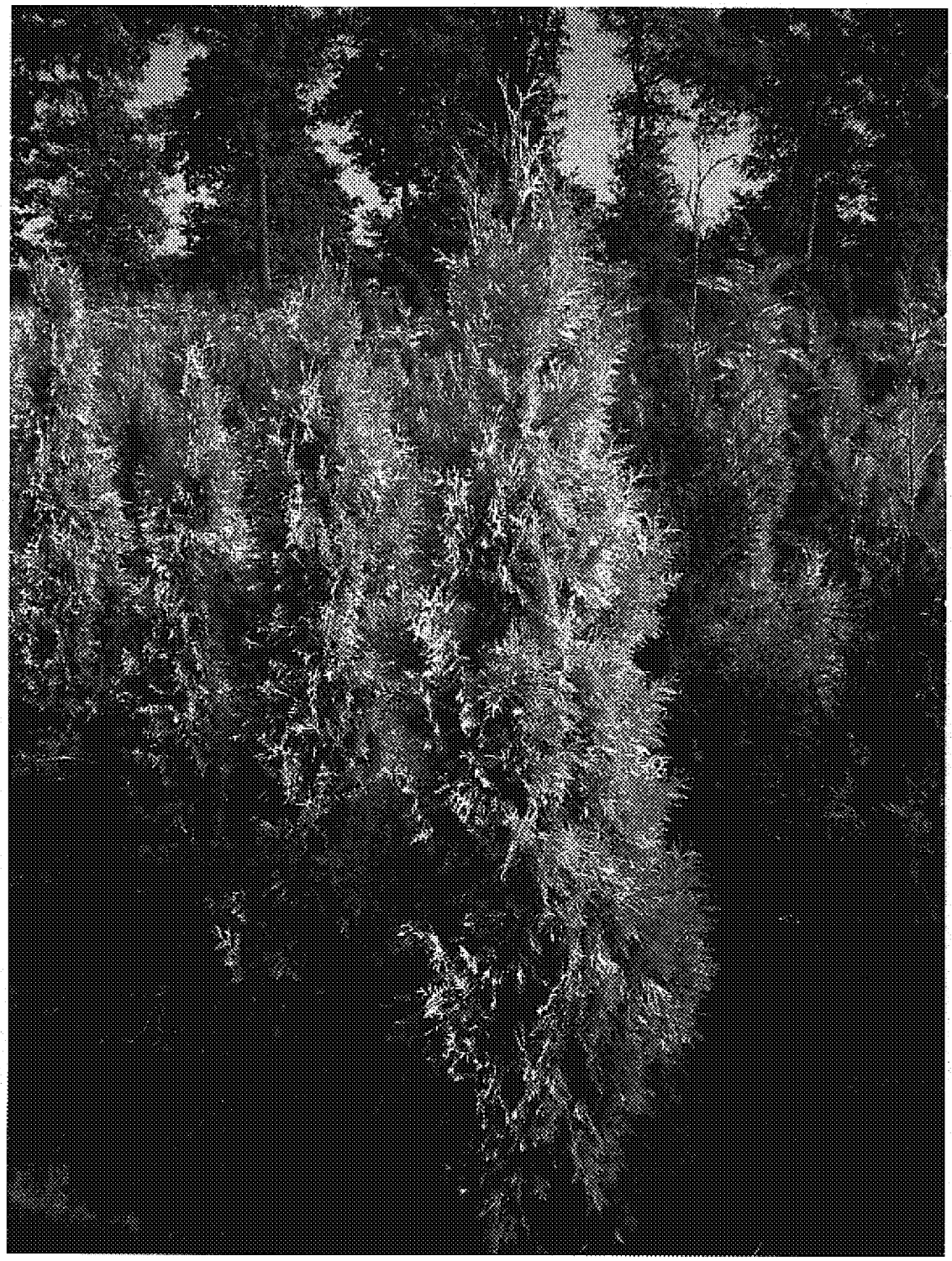
Figure 2:
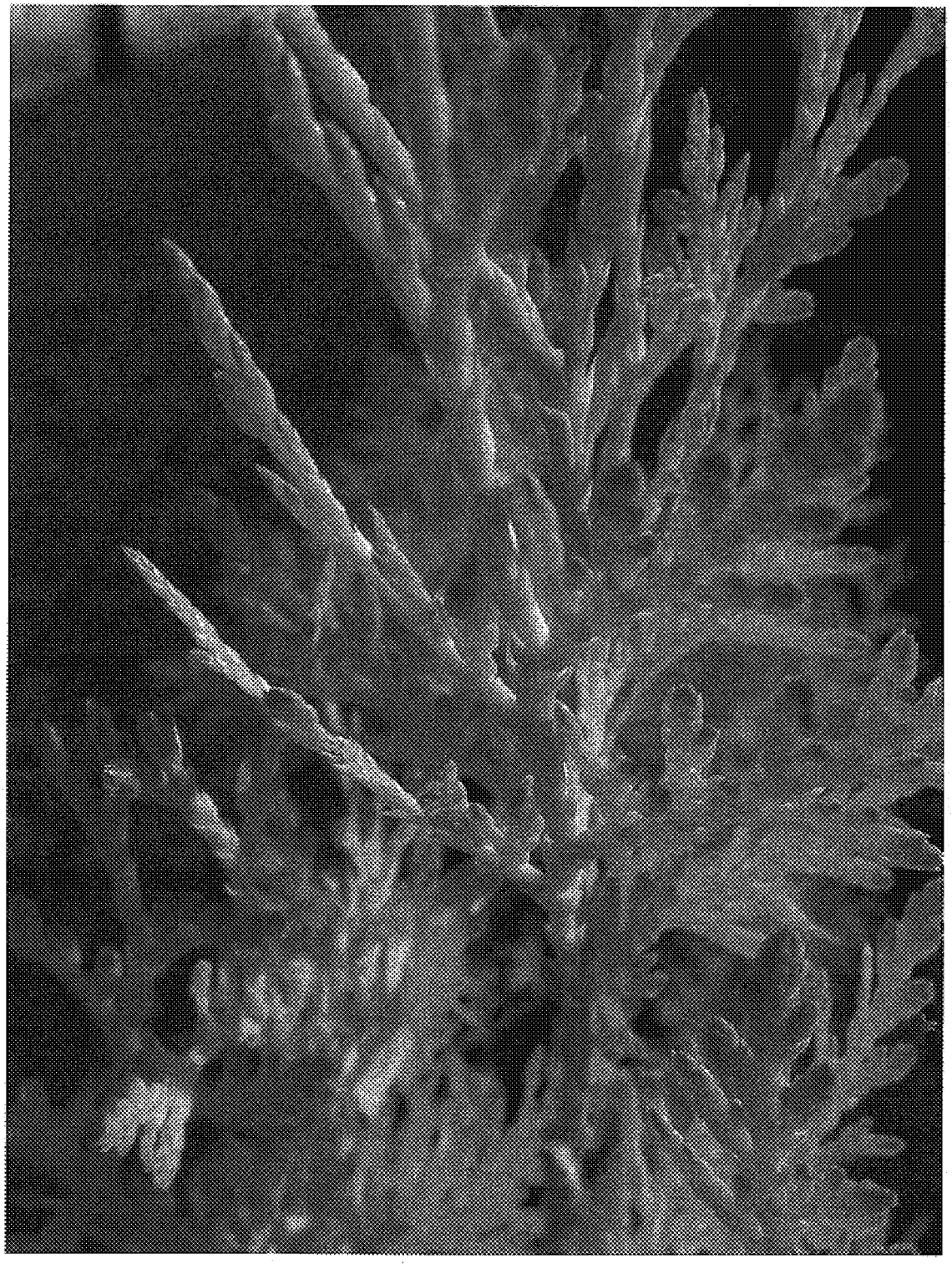

The drawing labeled as FIG. 2 illustrates a close-up view of the foliage of 'Daniëllow'.

BOTANICAL DESCRIPTION OF THE PLANT

The following is a detailed description of 'Daniëllow'. Botanical data was collected during the 2006 growing season from plants which were approximately two years old in a two liter container. The observed plants were growing out of doors in the ground in Nikerk, Netherlands. The color determinations have been made by reference to the 2001 edition of The Royal Horticultural Society Colour Chart, except where general color terms of ordinary dictionary significance are used.

Family: Cupressaceae.
Botanical classification: *Thuja plicata.*
Genus: *Thuja.*
Species: *plicata.*
Variety denomination: 'Daniëllow'.
Common name: Western Red Cedar.
Use: Landscape shrub.
Container size: Suggested container sizes for planting: 1, 3, 5 or 7 gallon.
Cultural requirements: Moist, well drained fertile soils. Light requirement: Full sun to partial shade.
Parentage: 'Daniëlow' is a naturally occurring mutation found on *Thuja plicata* 'Gelderland'.
Plant description:

*Plant habit.*—Upright and conical.
*Vigor.*—Moderately vigorous.
*Dimensions.*—An average of 46 cm in height and 24 cm in width.
*Growth rate.*—Approximately 25 cm per season in a young plant.
*Hardiness.*—USDA Zone 5–8.
*Root system.*—Fibrous.
*Propagation.*—Propagation is accomplished by semi hardwood to hardwood cuttings.
*Culture.*—Moist, well drained fertile soils in full sun to partial shade.
*Time to develop roots.*—From 6 to 8 weeks to initiate roots.
*Temperature for rooting.*—Rooting occurs when rooting medium is maintained within temperature range 16° C. to 28° C.
*Crop time.*—An established plant in a 1 gallon container takes an average one year to finish.
*Disease and pest susceptibility.*—'Daniëllow' is neither less nor more susceptible to pests or diseases than the species or in comparison to other cultivars of the species known to the inventor.

Branches:

*Branching habit.*—Main stems grow from base and have lateral branches.
*Basal branching.*—Yes.
*Number of lateral branches.*—An average of 15.
*Lateral branch dimensions.*—An average of 17.7 cm in length and 3 mm in diameter.
*Internode length.*—An average of 1.7 cm.
*Stem.*—Appearance: Rounded, covered with scale-like leaves, dull. Aspect: Rounded, covered with scale-like leaves. Strength: Strong. Color: N167A and N167B; older bark N200B and N200C. Pubescence: None.

Foliage:

*Arrangement.*—Opposite.
*Durability to stress.*—Strong.
*Quantity of leaves per lateral branch.*—An average of 2000 scale-like leaves.
*Leaf.*—Shape: Scale-like; oblanceolate. Tip: Apiculate. Base: Cuneate. Dimensions: An average of 6.5 mm in length and 2.5 mm in width. Texture: Slightly glossy. Pubescence: None. Margin: Entire. Venation: Not visible. Color, young leaf (abaxial and adaxial surface): 145A. Color, mature leaf (abaxial surface): 8B. Color, mature leaf (adaxial surface): 6C and 7C. Attachment: Sessile. Petiole: None.
*Fragrance.*—When crushed, resinous typical of *Thuja plicata.*

Flowers: No flowers have been observed.
Seeds: No seeds have been observed.

What is claimed is:

1. A new and distinct cultivar of *Thuja* plant named 'Daniëllow' as described and illustrated herein.

* * * * *